(12) United States Patent
Haeckl et al.

(10) Patent No.: US 8,617,056 B2
(45) Date of Patent: Dec. 31, 2013

(54) ENDOSCOPE

(75) Inventors: Norbert Haeckl, Leibertingen (DE);
Daniel Seeh, Immendingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 350 days.

(21) Appl. No.: 13/034,290

(22) Filed: Feb. 24, 2011

(65) Prior Publication Data
US 2011/0208001 A1   Aug. 25, 2011

(30) Foreign Application Priority Data

Feb. 25, 2010   (DE) .......................... 10 2010 002 334

(51) Int. Cl.
*A61B 1/00* (2006.01)
*A61B 1/04* (2006.01)
*A61B 1/06* (2006.01)

(52) U.S. Cl.
USPC ............................ 600/127; 600/129; 600/175

(58) Field of Classification Search
USPC ......... 600/121–125, 127, 129, 136, 139–144, 600/146, 149, 175
See application file for complete search history.

(56) References Cited

U.S. PATENT DOCUMENTS

| | | |
|---|---|---|
| 3,190,286 A | 6/1965 | Stokes |
| 4,726,355 A | 2/1988 | Okada |
| 4,807,598 A | 2/1989 | Hasegawa |
| 4,867,136 A | 9/1989 | Suzuki et al. |
| 5,536,235 A | 7/1996 | Yabe et al. |
| 5,735,793 A | 4/1998 | Takahashi et al. |
| 6,095,970 A * | 8/2000 | Hidaka et al. ................ 600/110 |
| 7,766,821 B2 | 8/2010 | Brunnen |
| 8,317,684 B2 * | 11/2012 | Matsuo et al. ................ 600/140 |
| 2008/0097160 A1 | 4/2008 | Salvermoser et al. |
| 2009/0171158 A1 | 7/2009 | Matsuo et al. |

FOREIGN PATENT DOCUMENTS

| | | |
|---|---|---|
| EP | 0 027 185 | 4/1981 |
| EP | 0 535 847 | 4/1993 |
| EP | 1 661 505 | 5/2006 |
| JP | 2006-006761 A | 1/2006 |
| JP | 2006-334271 A | 12/2006 |
| JP | 2009-045134 A | 3/2009 |
| WO | WO 2009/005276 | 1/2009 |

OTHER PUBLICATIONS

English translation of search report for the German priority application (102010002334.5) to the instant application, Sep. 3, 2010, 4 pages.

* cited by examiner

*Primary Examiner* — Alireza Nia
(74) *Attorney, Agent, or Firm* — Skaar Ulbrich Macari, P.A.

(57) ABSTRACT

Provided is an endoscope with a handle and an endoscope shaft connected to the handle, which has a bendable section and a rigid section, adjoining it, with a support extending in the longitudinal direction of the endoscope shaft, wherein the bendable section has a flexible outer tube the end of which facing the rigid section rests on the support, wherein a fixing sleeve is connected to the end section and covers the end of the outer tube facing the rigid section such that said end is clamped for fixing between the fixing sleeve and the support.

9 Claims, 2 Drawing Sheets

ENDOSCOPE

PRIORITY

The present application claims priority to German Application No. 102010002334.5, filed Feb. 25, 2010, which is hereby incorporated by reference in its entirety.

FIELD

The invention relates to endoscopes, and more particularly, to endoscopes having improved durability.

BACKGROUND

It was previously customary for endoscopes to wrap the distal end of the outer tube thereof in a yarn or fibre in order to thereby fix it to the support. However, such a type of fixing is not durable. In particular, this type of fixing withstands only a limited number of autoclaving cycles.

SUMMARY

Starting from this, the object of the invention is to provide for an improved endoscope wherein the fixing of the distal end of the outer tube to the support can be guaranteed in a durable manner, even if the endoscope is frequently autoclaved.

The object is achieved according to certain embodiments, by connecting a fixing sleeve to the rigid section that covers the end of the outer tube which faces the rigid section and which is clamped for fixing between the fixing sleeve and the support. The end of the outer tube facing the rigid section is thus clamped between the fixing sleeve and the support, whereby a durable fixing can be guaranteed. This type of clamping also withstands a large number of autoclaving cycles. By autoclaving is meant in particular here that the endoscope or the endoscope shaft is exposed to saturated water vapour of approx. 120° C.-140° C. for at least several minutes for sterilization. The endoscope can thus be sterilized, which is important in particular for medical applications.

The fixing sleeve can be mounted, screwable, on the rigid section in the longitudinal direction of the endoscope shaft. It is thus possible to screw the fixing sleeve onto the end section and to thereby realize the desired clamping. Naturally, any other type of connection between the fixing sleeve and the rigid section is also possible and within the scope of the invention. In particular, the fixing sleeve can be glued, soldered, etc. to the rigid section.

The fixing sleeve can have a fixing area with a tapering internal diameter. The distance between the fixing sleeve and the support thereby reduces in axial direction, whereby the clamping force that acts on the distal end of the outer tube increases in axial direction. This naturally leads to a better fixing. In particular, the support can have a first area with an external diameter increasing in the direction away from the bendable section. The fixing area of the fixing sleeve can lie opposite the first area of the first support. This leads to a further reduction of the distance between fixing sleeve and support, with the result that a further increase in the clamping force is achieved.

The support can furthermore have a second area, adjoining the first area, with an increasing external diameter in the direction away from the bendable section. Thus, although the distance between the support (in the area of the second area) and the fixing sleeve increases again, this leads overall to an improvement in respect of the resistance of the clamping to tensile forces axially acting on the outer tube.

In one preferred embodiment, a housing sleeve which has a support area forming the support can be fastened to the rigid section of the shaft. The production of the endoscope can thereby be simplified. In particular, the housing sleeve can be more easily adapted to the special requirements of the respective endoscope.

Furthermore, the housing sleeve can have a fastening area to which the fixing sleeve is directly connected. The fastening area can in particular be an external thread, with the result that the fixing sleeve can be screwed onto the fastening area.

With the endoscope according to certain embodiments of the invention, the end of the outer tube facing the rigid section can be wrapped in a fibre or yarn which presses the end facing the rigid section onto the support. Furthermore, the yarn or fibre can additionally be impregnated or loaded with an adhesive, such as e.g. a resin. A further increase in the fixing is thereby achieved.

By the rigid section of the endoscope shaft is meant here a section which, unlike the bendable section, cannot be bent. Naturally, the rigid or stiff section has a degree of elasticity, with the result that a degree of bending is possible. However, it is not bendable in the same way as the bendable section which can be bent reproducibly via actuating elements on the handle.

The rigid section can be a section of the endoscope shaft that is connected to the distal or proximal end of the bendable section. In particular, the rigid section can be the distal end section of the endoscope shaft. The distal end section can e.g. contain an imaging optics for imaging the desired areas. An image sensor onto which the imaging optics images the image can also be contained in the distal end section. Alternatively, it is possible that a transmission optics which passes through the bendable section as far as the handle of the endoscope is arranged downstream of the imaging optics.

The endoscope according to certain embodiments of the invention or at least the endoscope shaft of the endoscope according to certain embodiments of the invention is designed hermetically sealed and can therefore be autoclaved.

Furthermore, with the endoscope according to certain embodiments of the invention, the endoscope shaft can have, between the handle and the bendable section, a rigid main part which is connected to the bendable section, wherein the main part has a second support extending in the longitudinal direction of the endoscope shaft, on which the proximal end of the flexible outer tube rests, wherein a second fixing sleeve is connected to the main part and covers the proximal end of the outer tube, which is clamped for fixing between the second fixing sleeve and the second support. Thus, the other end (the proximal end which points towards the handle of the endoscope) of the outer tube can thereby also be fixed satisfactorily and durably to the main part.

The second fixing sleeve as well as the second support can be formed in the same way as the fixing sleeve and the support for fixing the distal end of the outer tube.

The endoscope according to certain embodiments of the invention can also contain further elements or components known to a person skilled in the art which are necessary to operate the endoscope. In particular, further components can be provided in or attached to the handle.

The endoscope according to certain embodiments of the invention is a medical endoscope.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

DETAILED DESCRIPTION

In the following descriptions, the present invention will be explained with reference to example embodiments thereof. However, these example embodiments are not intended to limit the present invention to any specific example, environment, embodiment, applications or particular implementations described in these example embodiments. Therefore, descriptions of these example embodiments are only for purposes of illustration rather than limitation to the invention. It should be appreciated that in the following example embodiments and the attached drawings, elements unrelated to the present invention are omitted from depiction; and dimensional relationships among individual elements in the attached drawings are illustrated only for ease of understanding, but not to limit the actual scale.

Figure 1:
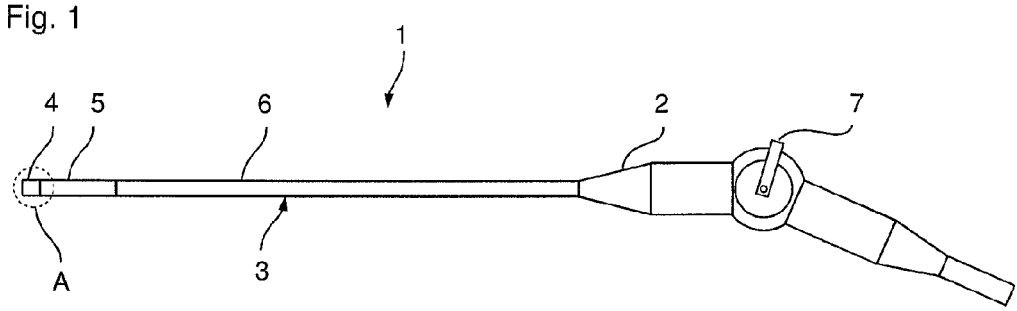
FIG. 1 is a side view of an embodiment of the endoscope according to the invention.
Figure 2:
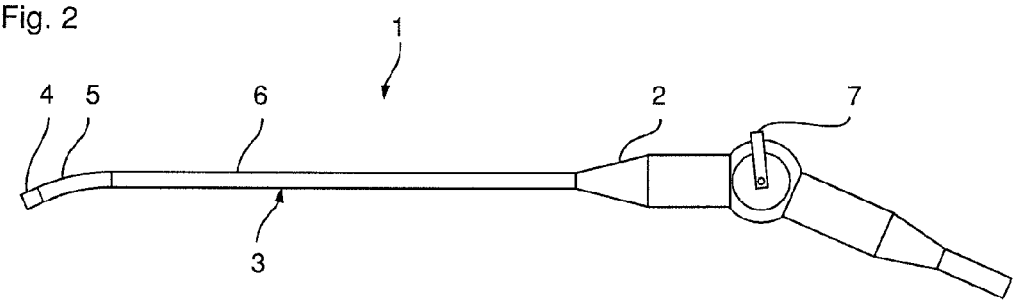
FIG. 2 is a side view of the endoscope from FIG. 1 with a distal end section of the endoscope shaft pivoted downwards.

In the embodiment shown in FIGS. 1 to 4, the endoscope 1 according to the invention comprises a handle 2 and a shaft 3 connected to the handle 2. The shaft 3 is designed over almost its entire length as a rigid shaft 3, wherein a rigid distal end section 4 is connected, articulated, to a rigid main part 6 of the shaft 3 over a bendable section 5, with the result that the distal end section 4 is pivotable relative to the remaining part 6. As is indicated in FIG. 2, e.g. the distal end section 4 can be turned downwards by pivoting a control lever 7 on the handle 2 from the position shown in FIG. 1 into the position shown in FIG. 2.

In order to achieve the desired flexibility, the bendable section 5 has several pipe segments connected, articulated, to each other which, to simplify the representation, are not shown. The precise design of such pipe segments is known to a person skilled in the art and will not be described in detail. As an example of a possible design of the pipe segments, reference is made to DE 10 2004 027 850 A1 and US 2005/0272978 A1, the content of each of which is hereby incorporated by reference in the present description. The pipe segments can e.g. be designed according to FIGS. 11A-11C of these incorporated references.

The bendable section 5 can also be actuated in the same way as in DE 10 2004 027 850 A1 and US 2005/0272978 A1 via the control wires (not shown), wherein here the control wires are connected to the control lever 7. The end section 4 can thus be pivoted downwards (as shown in FIG. 2) and upwards (not shown) via the control lever 7. The bendable section 5 can here be designed in particular such that a pivoting of the end section 4 perpendicular to the plane of drawing according to FIGS. 1 and 2 is also possible. For this, a second control lever (not shown) is then provided on the handle 2, in order to carry out this pivoting movement.

The bendable section 5 furthermore has a flexible outer tube 11 which is connected to the distal end section 4 such that a hermetically sealed sheath is provided for the pipe segments and all the elements contained therein.

Figure 3:
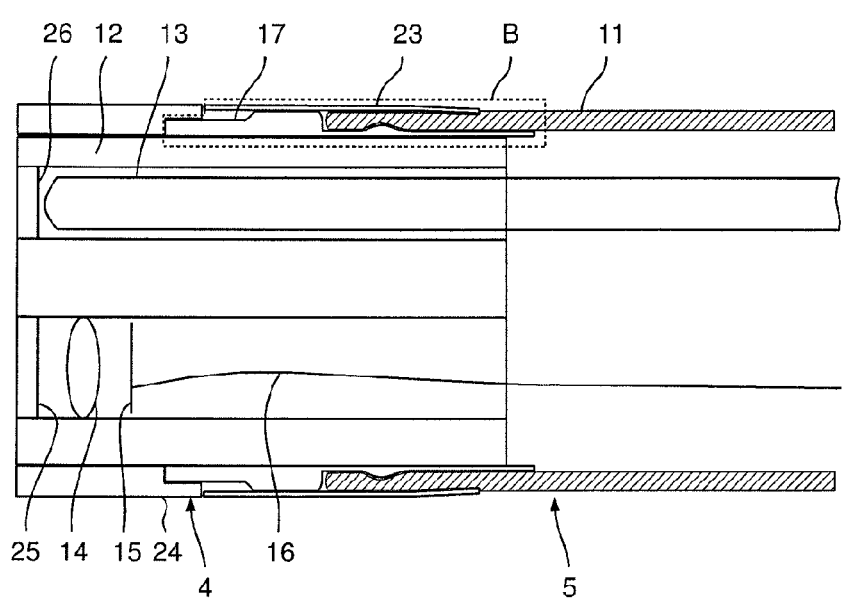
FIG. 3 is an enlarged sectional representation of the detail A from FIG. 1.
Figure 4:
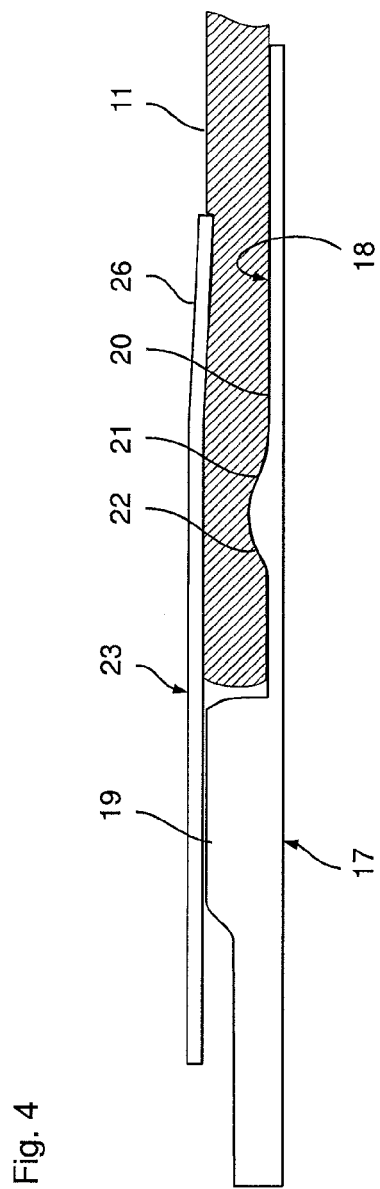
FIG. 4 is an enlarged view of the detail B from FIG. 3.

As can be seen from the enlarged sectional representation of the detail A from FIG. 1 in FIG. 3, the distal end section 4 has a main body 12 in which an optical fibre bundle 13, running through the bendable section 5, for illumination ends and in which a recording lens system 14 for recording the desired images is arranged. The recording lens system 14 is represented here schematically as a lens which projects the image onto an image sensor 15. The electrical image signals of the image sensor 15 are transmitted to the handle 2 via a cable 16 running through the bendable section 5 and the main part 6.

Alternatively, it is possible that a light guide system (not shown) extending through the bendable section 5 and the main part 6, which transmits the recorded image to the handle 2, is arranged downstream of the recording lens system 14.

In the sectional representation of FIG. 3, to simplify the representation, only the outer tube 11 is drawn hatched. A housing sleeve 17 which, as can best be seen in FIG. 4, has a support area 18 and a fastening area 19, adjoining it, with an external thread is fastened to the main body 12. The detail B from FIG. 3 is represented enlarged in FIG. 4. The support area 18 has, starting from its end pointing towards the bendable section 5 in the direction to the end section 4, an area 20 with a constant external diameter which then passes into an area 21 with an increasing external diameter to which an area 22 with a decreasing external diameter joins which extends to the fastening area 19. The outer tube 11 rests on the areas 20 to 22.

A fixing sleeve 23 which, when screwed on, extends over the areas 21 and 22 as well as partially over the area 20 of the housing sleeve 17 and thereby covers the end of the outer tube 11 facing the end section or rests on its outside and thus presses the end facing the end section against the housing sleeve 17 is screwed onto the fastening area 19 of the housing sleeve 17. In this way, the outer tube 11 is clamped between housing sleeve 17 and fixing sleeve 23.

The fixing sleeve 23 is here designed such that its internal diameter decreases in the direction to the bendable section 5, with the result that the distance between fixing sleeve 23 and housing sleeve 17 also becomes smaller in the direction to the bendable section 5. This leads to a satisfactory fixing of the outer tube 11 on the housing sleeve 17. The area of the fixing sleeve 23 in which the internal diameter reduces can also be called fixing area 26.

The areas 21 and 22 of the housing sleeve 17 form a local elevation, with the result that the distance between the fixing sleeve 23 and the housing sleeve 17 in front of and behind the local increase (in axial direction; from right to left in FIG. 4) is greater than in the area of the local increase. The flexible outer tube 11 is thus compressed most strongly in this area, whereby the clamping of the outer tube 11 withstands higher axial tensile forces acting on the outer tube 11.

In particular, the clamping of the outer tube 11 brought about by the housing sleeve 17 and the fixing sleeve 23 is hermetically sealed. Even a large number of autoclaving cycles do not lead to leaks, with the result that an excellent fixing of the outer tube 11 to the distal end section 4 is provided that is mechanically extremely stable and can be autoclaved in a durable manner.

In a development, it is possible that, before the fixing sleeve 23 is screwed on, the distal end section of the outer tube 11 resting on the support area 18 is wrapped in a yarn or fibre (for example nylon yarn) and it is thereby pressed against the support area 18. The yarn or fibre can additionally be impregnated or loaded with an adhesive (for example glue, resin, etc.), with the result that a further improvement of the fixing is achieved. The fixing sleeve 23 then lies over this fibre or yarn, which leads to a further improvement of the fixing.

The described fixing of the outer tube 11 can be carried out in the same way for the proximal end of the outer tube 11, in order to connect it to the main part 6. For example, the housing sleeve 17 shown in FIG. 4 as well as the fixing sleeve 23 can be used. In this manner, a hermetically sealed connection of the flexible outer tube 11 both to the distal end section 4 and to the main part 6 is possible.

Naturally, the housing sleeve 17 which is fastened to the main body 12 by means of a fastening sleeve 24 according to the representation in FIG. 3 need not be a separate component. It is also possible that the housing sleeve is integrated in one piece into the main body 12 or into the main part 6.

The outer tube 11 is preferably made of an elastic polymer (e.g. a fluoroelastomer). Naturally, any other elastic material or combination of materials can be used, wherein materials that can be autoclaved are preferred. The rigid elements of the shaft 3 and in particular the fixing sleeve 23 as well as the housing sleeve 17 can be made of a metal or a metal alloy. Stainless steel is preferably used.

The endoscope 1 according to the invention can also have further elements known to a person skilled in the art which are necessary for operation. Thus, the endoscope 1 described here in connection with FIGS. 1 to 4 can be autoclaved. For this, e.g. cover glasses 25 and 26 are arranged in the main body 12 in front of the projection lens system 14 as well as the optical fibre bundle 13, in order to achieve the desired hermetic seal. The cover glasses 25, 26 are preferably made of sapphire glass.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:
1. An endoscope comprising:
   a handle;
   an endoscope shaft having proximal and distal ends, the proximal end connected to the handle, the endoscope shaft comprising:
      a bendable section, including a flexible outer tube having a distal end portion, an inside surface and an outside surface;
      a rigid section adjoining the distal end portion of the flexible outer tube, the rigid section including a support extending in the longitudinal direction of the endoscope shaft towards the proximal end of the endoscope shaft,
      wherein the inside surface of the distal end portion of the flexible outer tube contacts the support; and
   a fixing sleeve, connected to the rigid section and extending over the outside surface of the of the distal end portion of the flexible outer tube such that the distal end portion of the flexible outer tube is secured between the fixing sleeve and the support,
   wherein the fixing sleeve includes a first fixing region having a gradually tapered converging internal diameter, and wherein the support includes a second fixing region having a diverging portion wherein an outside diameter of the support increases gradually in the longitudinal direction towards the distal end of the shaft from a first diameter to a maximum diameter and a converging portion adjoining the diverging portion wherein the outside diameter of the support gradually decreases in the longitudinal direction towards the distal end of the shaft from the maximum diameter to a second diameter.

2. The endoscope according to claim 1, wherein the fixing sleeve is screwably mounted on the rigid section in the longitudinal direction of the endoscope shaft.

3. The endoscope according to claim 1, wherein the first fixing region contacts the outer surface of the flexible outer tube opposite the location where the second fixing region contacts the inside surface of the flexible outer tube.

4. The endoscope according to claim 1, wherein the first fixing region of the fixing sleeve lies opposite the diverging portion of the support.

5. The endoscope according to claim 1, further comprising a housing sleeve fastened to the rigid section, the housing sleeve including a support area forming the support.

6. The endoscope according to claim 5, wherein the housing sleeve includes a fastening area to which the fixing sleeve is directly connected.

7. The endoscope according to claim 1, wherein the rigid section comprises the distal end portion of the endoscope shaft.

8. The endoscope according to claim 7, wherein the endoscope shaft further comprises a rigid main part disposed between the handle and the bendable section, the rigid main part connected to the bendable section, wherein the rigid main part comprises a second support extending along a longitudinal direction of the endoscope shaft, on which a proximal end of the flexible outer tube rests, and wherein a second fixing sleeve is connected to the rigid main part and covers the proximal end of the flexible outer tube, such that said proximal end is secured between the second fixing sleeve and the second support.

9. The endoscope according to claim 1, wherein the first diameter and the second diameter are the same.

* * * * *